United States Patent [19]

Hansen et al.

[11] Patent Number: 5,705,158

[45] Date of Patent: *Jan. 6, 1998

[54] TREATMENT OF INFECTIOUS AND INFLAMMATORY LESIONS

[75] Inventors: Hans John Hansen, Westfield; Milton David Goldenberg, Short Hills, both of N.J.

[73] Assignee: Immunomedics, Inc., Morris Plains, N.J.

[*] Notice: The term of this patent shall not extend beyond the expiration date of Pat. No. 5,439,665.

[21] Appl. No.: 469,992

[22] Filed: Jun. 6, 1995

Related U.S. Application Data

[63] Continuation of Ser. No. 13,206, Feb. 1, 1993, which is a continuation of Ser. No. 466,873, Feb. 23, 1990, abandoned, which is a division of Ser. No. 226,180, Jul. 29, 1988, Pat. No. 4,925,648.

[51] Int. Cl.[6] .................. A61K 39/395; A61K 49/00; C07K 16/18

[52] U.S. Cl. .................... 424/181.1; 424/182.1; 424/154.1; 424/179.1; 530/387.1; 530/391.1; 530/391.3; 530/388.1; 530/388.73; 530/38.75; 530/391.7

[58] Field of Search .................. 530/387.1, 388.73, 530/388.75, 391.1, 391.5, 391.7, 391.3, 388.1; 424/181.1, 182.1, 154.1, 179.1

[56] References Cited

U.S. PATENT DOCUMENTS

| | | | |
|---|---|---|---|
| 4,634,586 | 1/1987 | Goodwin et al. | 424/1.1 |
| 4,834,976 | 5/1989 | Rosok et al. | 424/87 |
| 4,925,648 | 5/1990 | Hansen et al. | 424/1.1 |
| 5,332,567 | 7/1994 | Goldenberg | 424/1.49 |
| 5,439,665 | 8/1995 | Hansen et al. | 424/1.49 |

OTHER PUBLICATIONS

Koizumi, M. et al, Cancer Research, 48:1189–1194, Mar. 1, 1988.
Goodman & Gilman, The Pharmacological Basis of Therapeutics, 6th ed., Eds. pp. 1080–1248, Macmillan Publishing Co, N.Y, 1980.

Primary Examiner—Susan A. Loring
Attorney, Agent, or Firm—Foley & Lardner

[57] ABSTRACT

A polyspecific anti-leukocyte antibody conjugate for targeting foci of leukocyte accretion comprises an immunoreactive polyspecific composite of at least two different substantially monospecific antibodies or antibody fragments, conjugated to at least one imaging agent, wherein at least two of said antibodies or antibody fragments specifically bind to different leukocyte cell types.

A method for targeting an imaging agent to an inflammatory or infectious lesion comprises injecting a mammal parenterally with an effective amount for targeting of the above anti-leukocyte imaging conjugate.

A therapeutic anti-leukocyte antibody-agent conjugate for targeting foci of leukocyte accretion comprises at least one immunoreactive substantially monospecific antibody or antibody fragment which specifically binds to at least one leukocyte cell type, conjugated to at least one therapeutic antimicrobial agent.

A method of treatment of an infectious lesion comprises injecting a mammal parenterally with an effective amount for therapy of the above anti-leukocyte therapeutic conjugate.

16 Claims, No Drawings

1

TREATMENT OF INFECTIOUS AND INFLAMMATORY LESIONS

This application is a continuation of U.S. Ser. No. 08/013,206, filed Feb. 1, 1993, which is a continuation of U.S. Ser. No. 07/466,873, filed Feb. 23, 1990, now abandoned, which is a divisional of U.S. application Ser. No. 07/226,180, filed Jul. 29, 1988, now U.S. Pat. No. 4,925,648.

BACKGROUND OF THE INVENTION

This invention relates to reagents and methods for targeting at least one diagnostic or therapeutic agent to an inflammatory or infectious lesion. Polyspecific antibody composites specific for at least two different leukocyte cell types are conjugated to at least one diagnostic or therapeutic agent for use in the present invention.

It has been recognized that, since leukocytes accumulate in large numbers at localized sites of infection or inflammation, it might be feasible to detect such sites by removing leukocytes from the blood, labeling them with an appropriate indicator, conventionally In-111, and returning them to the blood. After a period of time has passed sufficient to allow the labeled leukocytes to redistribute in the body, the subject is scanned with suitable equipment to detect localization of the labeled leukocytes. While effective, the method described above is substantially time consuming since time is required for the leukocyte separation, labeling and, particularly redistribution in the body after re-injection.

In U.S. Pat. No. 4,634,586 (Goodwin et al.), incorporated herein by reference in its entirety, leukocytes are radioimmunoimaged by injecting patients with an immunoreactive nonleukocidal conjugate of an anti-leukocyte monospecific antibody and a gamma emitting radioactive metal chelate, waiting for the conjugate to localize on the leukocytes, injecting a patient with an antibody to the conjugate to clear the blood of background nonlocalized conjugate, and visualizing the leukocytes by scintillation scanning.

Leukocyte imaging has been severely limited in the prior art due to poor target to background ratio. It has been shown that the localization ratio can be increased by using second antibody clearance. However, the target to background ratio remains a problem, because each targeting antibody only binds to a specific leukocyte cell type, either a granulocyte, a monocyte, a B-lymphocyte or a T-lymphocyte. Therefore, there will be many antibodies that are highly reactive and specific for a particular leukocyte cell in the background that have not bound to the target site, because that particular leukocyte cell type is not present in appreciable concentration at the site of infection or inflammation.

A need therefore continues to exist for a method of targeting an imaging or therapy agent to an inflammatory or infectious lesion with higher efficiency and enhanced target to background ratio to permit more effective detection and/or treatment of the lesion.

OBJECTS OF THE INVENTION

One object of the present invention is to provide a polyspecific antibody-agent conjugate which selectively binds to at least two different leukocyte cell types, for targeting inflammations or infectious lesions with an enhanced target to background ratio.

Another object of the present invention is to provide a method for targeting a polyspecific antibody-agent conjugate to an infectious or inflammatory lesion with higher efficiency and an enhanced target to background ratio.

A further object of the invention is to provide reagents and methods for more efficient detection and/or therapy of infectious and inflammatory lesions.

Other objects of the present invention will become more apparent to those of ordinary skill in the art in light of the following discussion.

SUMMARY OF THE INVENTION

These and other objects of the present invention are achieved by providing a polyspecific antibody-agent conjugate for targeting foci of leukocyte accretion, comprising an immunoreactive polyspecific composite of at least two different substantially monospecific antibodies or antibody fragments, conjugated to at least one imaging agent, wherein at least two of said antibodies or antibody fragments specifically bind to different leukocyte cell types.

The invention also provides a method for targeting a diagnostic agent to an inflammatory or infectious lesion which comprises injecting a mammal parenterally with an effective amount for targeting of the polyspecific antibody-agent conjugate.

The invention further provides an anti-leukocyte antibody-agent conjugate for targeting and treating an infectious lesion containing a focus of leukocyte accretion, comprising at least one immunoreactive substantially monospecific antibody or antibody fragment which specifically binds to at least one leukocyte cell type, conjugated to at least one therapeutic antimicrobial agent.

A method for treating infectious lesions is also provided, comprising parenterally injecting a therapeutically effective amount of the foregoing conjugate in a patient with such a lesion. Polyspecific anti-leukocyte antibody/fragment mixtures and/or composites also can be used as targeting vehicles for therapy according to the invention.

In addition, the present invention provides sterile injectable preparations and kits for use in practicing the foregoing method.

DETAILED DESCRIPTION OF THE INVENTION

The present invention provides an improvement over the prior art imaging method of Goodwin et al. through the use of a polyspecific antibody-agent conjugate for targeting loci of leukocyte accretion. Different leukocyte cell types (e.g., granulocytes, monocytes, T- and B-lymphocytes) that are involved in the development of an infectious or inflammatory lesion are often present in markedly different ratios in the inflammatory or infectious lesion, depending upon the nature of the agent that initiates the development of the lesion and/or on the age of the lesion. Use of a monospecific antibody, as taught by Goodwin, will result in inefficient targeting of the lesion if only a portion of the leukocyte population at the site of the lesion bind the targeting antibody, and this will reduce the target to background ratio (also called "localization ratio"). Use of a mixture of antibodies with different leukocyte specificities can improve the percentage of injected dose reaching the target site if the right proportion of specificities is used, but can further increase binding to non-target leukocytes if the lesion contains primarily a single leukocyte cell type.

The present invention resolves this dilemma by using a polyspecific targeting antibody composite which is able to bind to two or more different leukocyte cell types. The imaging agent component of the antibody-agent conjugate is thereby localized at the target site with higher efficiency and an enhanced target to background ratio, regardless of the mix of leukocyte cell types.

The polyspecific targeting antibody composite comprises at least two different substantially monospecific antibodies or antibody fragments, wherein at least two of the antibodies or antibody fragments specifically bind to different leukocyte cell types. Thus, at least one antigen binding site on the composite will bind to a first leukocyte cell type while at least a second antigen binding site on the same targeting composite will bind to a different leukocyte cell type. Such a composite will be denoted an "anti-leukocyte composite" herein. The antibody composite may also contain antibodies and/or fragments that bind to two or more different antigens or epitopes of the same antigen on the same leukocyte cell type. The leukocyte cell types include granulocytes, monocytes, B-lymphocytes and T-lymphocytes.

The immunological profile of the substantially monospecific, preferably monoclonal, antibodies used to make the composite of the present invention can be adjusted to ensure optimal binding to infectious or inflammatory lesions and minimal binding to nontarget sites. Depending upon the diagnostic use to which the reagent is to be put, the mix of leukocyte cell type specificities, antigen specificities and specificities for epitopes on antigens present on particular cell types, as well as of binding constants for the target antigens and/or cell types, all can be used to fine tune the selectivity and targeting efficiency of the reagent according to the invention.

Imaging reagents according to the invention can comprise bispecific, trispecific or, more generally, polyspecific antibody/fragment composites, conjugated to an imaging radioisotope or paramagnetic species. The antibody component of the conjugate can be made with whole antibodies or antibody fragments.

Use of term "antibody" herein will be understood to include antibody fragments and thus to be equivalent to the term "antibody/fragment" which is used interchangeably therefor in this discussion. Antibodies can be whole immunoglobulin of any class, e.g., IgG, IgM, IgA, IgD, IgE, chimeric antibodies or hybrid antibodies with dual or multiple antigen or epitope specificities, or fragments, e.g., F(ab')$_2$, F(ab)$_2$, Fab', Fab and the like, including hybrid fragments, and additionally includes any immunoglobulin or any natural, synthetic or genetically engineered protein that acts like an antibody by binding to a specific antigen to form a complex.

Antibodies can include antiserum preparations, preferably affinity purified by conventional procedures, e.g., by binding antigen to a chromatographic column packing, e.g., Sephadex, passing the antiserum through the column, thereby retaining specific antibodies and separating out other immunoglobulins and contaminants, and then recovering purified antibodies by elution with a chaotropic agent, optionally followed by further purification.

Monoclonal antibodies are also suitable for use in the present invention, and are preferred because of their high specificities. They are readily prepared by what are now generally considered conventional procedures for immunization of mammals with an immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention.

The present invention also envisions the use of antigen-specific fragments to create the polyspecific antibody-agent conjugate. Antibody fragments can be made by pepsin or papain digestion of whole immunoglobulins by conventional methods. It is known that antibody fragments may be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively an enzymatic cleavage using pepsin produces two monovalent Fab fragments and an Fc fragment directly. These methods are described, inter alia, by Goldenberg, in U.S. Pat. Nos. 4,036,945 and 4,331,647 and references contained therein, which patents are incorporated herein in their entireties by reference, and in Nisonoff et al, Arch. Biochem. Biophys., 89, 230 (1960); Porter, Biochem. J., 73, 119 (1959); and Edelman et al, in "Methods in Immunology and Immunochemistry", Vol. 1, 422 (Acad. Press, 1967), and are conventional in the art.

Other methods of cleaving antibodies, such as separation of heavy chains to form monovalent light-heavy chain fragments, further cleavage of fragments, or other enzymatic, chemical or genetic techniques may also be used, so long as the fragments retain specificity to the leukocyte against which their parent antibodies are raised.

Antibodies to leukocyte antigens may be made by inoculating a host with leukocytes from the patient species. For instance, antibodies for use in humans may be made by immunizing mice or other mammalian species with human leukocytes. Anti-human leukocyte serum may be collected from the host and affinity purified to provide polyclonal antibody for making the composite. Alternatively, splenocytes may be taken from the immunized host and fused with a suitable tumor cell line using somatic cell hybridization techniques to produce hybridomas that produce anti-leukocyte antibodies. These hybridomas may be isolated, subcloned and cultivated to produce monoclonal antibodies.

Monoclonal antibodies or fragments that recognize and bind to a leukocyte antigen are available commercially or may be made from somatic cell hybridization techniques described originally by Kohler, B. and Milstein, C., Nature (1975) 256:495–497 and reviewed at length in Monoclonal Antibodies, Kennett, T. J., et al, eds, Plenum (1980). Commercially available monoclonal antibodies to leukocyte antigens are represented by: OKT anti-T monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2: G7E11, W8E7, NKP15 and GO22 (Becton Dickinson); NEN9.4 (New England Nuclear); and FMC11 (Sera Labs).

The catalogue of Immunotech (Marseille, France, with worldwide distribution including Pel Freeze, Brown Deer, Wis., USA) lists commercially available monoclonal anti-leukocyte antibodies, many of which are suitable for preparing composites or therapy reagents according to the present invention. These include antibodies that specifically bind to T-cells, activated T-cells, B-cells, monocytes and granulocytes, including sub-populations thereof. Certain of the antibodies bind to antigens common to more than one type of leukocyte, e.g., monocytes and granulocytes, B-cells and granulocytes, T-cells and B-cells, T-cells and granulocytes, T-cells and monocytes and granulocytes and b-cells, and the like. The antibodies produced and distributed by Immunotech are similar to other antibodies from clones available elsewhere.

Suitable anti-T-cell antibodies include antibodies which bind to the CD1, CD2, CD4, CD6, CD7 or CD8 antigens. Preferred anti-T-cell antibodies are those that bind to the CD3 antigen and the CD5 antigen. A preferred antibody that binds to both monocyte and granulocyte antigens is a monoclonal which binds in particular to the CDW14 antigen. Preferred antibodies that bind to B-cells include antibodies that bind to the CD19 or CD21 antigens. Antibodies that bind to activated T-cells include monoclonals that bind to the CD25 or CD26 antigens. The CD antigens are leukocyte determinants that define antibodies having particular leukocyte specificities. A pair of antibodies that bind to the same epitope on the same CD antigen will cross-block binding to the same leukocyte cell types. Antibodies that bind specifically to the Ia (HLA-DR) histocompatibility antigen common to monocytes, B-lymphocytes and activated T-lymphocytes are classified as anti-HLA-DR Class II antibodies, and are of particular utility for certain applications.

The commercially available monoclonal antibodies to leukocyte antigens are typically of murine or rat origin and typically are IgGs or IgMs, although suitable antibodies for use in preparing conjugates according to the invention are not intended to be limited as regards species or Ig class. In general, antibodies can usually be raised to most antigens, using the many conventional techniques now well known in the art. Any antibody that binds to a leukocyte antigen which is found in sufficient concentration at a site of inflammation or infection in the body of a mammal can be used to make the targeting polyspecific antibody composite for use in the present invention.

It is generally desirable to use antibodies having a relatively high immunoreactivity, i.e., a binding constant of at least about $10^5$ l/mole, preferably at least about $10^7$ l/mole, and high immunospecificity, i.e. at least about 40%, preferably at least about 60%, more preferably at least about 70–95% for leukocyte antigens.

It may be preferable for certain applications to use antibodies having a somewhat lower binding constant in the present invention. Antibodies with high binding constants are likely to bind tightly not only to leukocytes at the site of inflammation or infection, but also to leukocytes present in the circulatory system, the marrow or normal tissues. On the other hand, antibodies with a lower binding constant will tend to accrete mainly at concentrated leukocyte foci at the site of a lesion, by virtue of a type of mass action effect. This will reduce premature clearance and nontarget accretion of the imaging label or, in therapy applications to be described below, the therapeutic agent, and thus increase the effective amount for targeting the lesion.

Antibody composites for imaging can be prepared by a variety of conventional procedures, ranging from simple glutaraldehyde linkage to more elegant and specific linkages between functional groups. The antibodies and/or antibody fragments are preferably covalently bound to one another, directly or through a short or long linker moiety, through one or more functional groups on the antibody/fragment, e.g., amine, carboxyl, phenyl, thiol or hydroxyl groups. Various conventional linkers in addition to glutaraldehyde can be used, e.g., disiocyanates, diisothiocyanates, bis (hydroxysuccinimide) esters, carbodiimides, maleimidehydroxysuccinimide esters and the like.

A simple, method is to mix the antibodies/fragments in the presence of glutaraldehyde to form the antibody composite. The initial Schiff base linkages can be stabilized, e.g., by borohydride reduction to secondary amines. This method is conventionally used to prepare other conjugates of proteins, e.g., peroxidase-antibody conjugates for immunohistochemical uses or for immunoassays. A diisothiocyanate or a carbodiimide can be used in place of glutaraldehyde as a non-site-specific linker.

Bispecific antibodies can be made by a variety of conventional methods, e.g., disulfide cleavage and reformation of mixtures of whole IgG or, preferably F(ab')$_2$ fragments, fusions of more than one clone to form polyomas that produce immunoglobulins having more than one specificity, and by genetic engineering. The bispecific antibodies can bind to one or more leukocyte cell types. Bispecific ("hybrid") antibody fragments have been prepared by oxidative linkage of Fab' fragments resulting from reductive cleavage of different antibodies. A portion of these will contain fragments specific to both of the antigens to which the original antibodies were raised. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of F(ab')$_2$ fragments including hybrid fragments containing a Fab' portion specific to each of the original antigens. Methods of preparing such hybrid antibody fragments are disclosed in Feteanu, "Labeled Antibodies in Biology and Medicine" pages 321–323 (McGraw-Hill Int. Bk. Co., New York et al, 1978); Nisonoff et al, Arch Biochem. Biophys., 93, 470 (1961); and Hammerling et al, J. Exp. Med., 128, 1461 (1968); and in U.S. Pat. No. 4,331,647.

More selective linkage can be achieved by using a heterobifunctional linker such as a maleimidehydroxysuccinimide ester. Reaction of the latter with an antibody/fragment will derivatize amine groups on the antibody/fragment, and the derivative can then be reacted with, e.g., an antibody Fab fragment with free sulfhydryl groups (or a larger fragment or intact immunoglobulin with sulfhydryl groups appended thereto by, e.g., Traut's Reagent). Such a linker is less likely to crosslink groups in the same antibody and improves the selectivity of the linkage.

It is advantageous to link the antibodies/fragments at sites remote from the antigen binding sites. This can be accomplished by, e.g., linkage to cleaved interchain sulfhydryl groups, as noted above. Another method involves reacting an antibody whose carbohydrate portion has been oxidized with another antibody which has at least one free amine function. This results in an initial Schiff base (imine) linkage, which is preferably stabilized by reduction to a secondary amine, e.g., by borohydride reduction, to form the final composite. Such site-specific linkages are disclosed, for small molecules or polypeptides or for solid phase polymer supports, in U.S. Pat. No. 4,671,958, and for larger addends in U.S. Pat. No. 4,699,784.

Included among the various types of bispecific antibody composites of the present invention are the following, which are particularly useful for certain applications: a composite of antibodies/fragments specific to monocytes and granulocytes for the detection and treatment of, e.g., osteomyelitis; a composite of antibodies/fragments specific to B-cells and monocytes for the detection and treatment of, e.g., Crohn's disease; a composite of antibodies/fragments specific to T-cells and B-cells for the detection and treatment of, e.g., sarcoidosis; a composite of antibodies/fragments specific to monocytes and lymphocytes for the detection and treatment of, e.g., tubercular lesions; and a composite of antibodies/fragments specific to the Ia(DR) histocompatibility antigen and granulocytes for the detection and treatment of infections associated with fever of unknown origin, e.g., granulomatous infections, tubercular lesions, fungal infections and the like.

Similar reactions can be used to bind a plurality of antibodies and/or antibody fragments, e.g., Fab or F(ab')$_2$ fragments, to one another to form polyspecific composites or composites with more than one epitopic specificity for a leukocyte cell type to increase its binding affinity or efficiency to the target lesion. Bispecific composites can be linked to an antibody/fragment specific to a third, fourth or further leukocyte cell type using, e.g., a heterobifunctional maleimide-hydroxysuccinimide ester linker to derivatize an amine group, followed by reaction of the derivative with a fragment having a free sulfhydryl group, optionally introduced with a reagent such as 2-iminothiolane. Alternative linkage modes will be readily apparent to the ordinary skilled artisan based on the disclosures for bispecific composite formation, and will require only minor variation and adaptation of such methods.

Included among the various types of trispecific or polyspecific antibody composites of the present invention are the following, which are particularly useful for certain applications: a composite of antibodies/fragments specific to T-cells, B-cells and monocytes for the detection and treatment of, e.g., graft rejection infiltrates; a composite of antibodies/fragments specific to B-cells, T-cells, monocytes and granulocytes for the detection and treatment of, e.g., chronic infection; a composite of antibodies/fragments specific to the Ia(DR) antigen, granulocytes and the T-1 antigen for the treatment of, e.g., thyroiditis, graft rejection infiltrates and tubercular lesions.

The antibody composite can be labeled with, or conjugated or adapted for conjugation to, a radioisotope for scintigraphic imaging or a magnetic resonance image enhancing agent, for use as a diagnostic imaging agent. Any conventional method of radiolabeling which is suitable for labeling proteins for in vivo use will be generally suitable for labeling the composite. This can be achieved by direct labeling with, e.g., a radioisotope of a halogen or a metal ion, using conventional techniques or more sophisticated methodologies, or by attaching a chelator for a radio-metal or paramagnetic ion. Such chelators and their modes of attachment to antibodies are well known to the ordinary skilled artisan and are disclosed inter alia in, e.g., Childs et al., J. Nuc. Med., 26:293 (1985); and in Goldenberg U.S. Pat. Nos. 4,331,647, 4,348,376, 4,361,544, 4,468,457, 4,444,744, and 4,624,846. Typical are derivatives of ethylenediaminetetraacetic acid (EDTA) and diethylenetriaminepentaacetic acid (DPTA). These typically have groups on the side chain by which the chelator can be attached to an antibody. Alternatively, carboxyl or amine groups on a chelator can be activated and then coupled to an antibody composite by well known methods. For example, deferoxamine, which is a chelator for Ga-67 has a free amine group that can be activated with a suitable linker to contain an activated carboxyl, isothiocyanate or like group, and then coupled to amines on an antibody composite.

The chelator may be bound to the antibody composite, directly or through a short or long chain linker moiety, through one or more functional groups on the antibody, e.g., amine, carboxyl, phenyl, thiol or hydroxyl groups. Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyanate linker disclosed in U.S. Pat. No. 4,680,338.

Labeling with either Iodine-131 (I-131) or Iodine-123 (I-123) is readily effected using an oxidative procedure wherein a mixture of radioactive potassium or sodium iodide and the antibody is treated with chloramine-T, e.g., as reported by Greenwood et al, Biochem. J., 89, 114 (1963) and modified by McConahey et al, Int. Arch. Allergy Appl. Immunol., 29, 185 (1969). This results in direct substitution of iodine atoms for hydrogen atoms on the antibody molecule, presumable on tyrosine residues, possibly also on tryptophan and even on phenylalanine residues, depending on the proportions of reagents and the reaction conditions. Alternatively, lactoperoxidase iodination may be used, as described by Feteanu, supra, page 303, and references cited therein.

Some more advanced methods of labeling are disclosed in pending applications U.S. Ser. Nos. 742,436 (Jun. 7, 1985), 084,544 (Aug. 12, 1987), and 176,421 (Apr. 1, 1988). The disclosures of all of the foregoing patents and applications are incorporated herein in their entireties by reference. A wide range of labeling techniques are disclosed in Feteanu, "Labeled Antibodies in Biology and Medicine", pages 214–309 (McGraw-Hill Int. Book Co., New York et al, 1978). The introduction of various metal radioisotopes may be accomplished according to the procedures of Wagner et al., J. Nucl. Med., 20,428 (1979); Sundberg et al, J. Med. Chem., 17, 1304 (1974); and Saha et al. J. Nucl. Med., 6, 542 (1976). The foregoing are merely illustrative of the many methods of radiolabeling proteins known to the art.

Examples of compounds useful for MRI image enhancement include paramagnetic ions, e.g., Gd(III), Eu(III), Dy(III), Pr(III), Pa(IV), Mn(II), Cr(III), Co(III), Fe(III), Cu(II), Ni(II), Ti(III) and V(IV) ions, or radicals, e.g., nitroxides, and these would be conjugated to a substrate bearing paramagnetic ion chelators or exposed chelating functional groups, e.g., SH, $NH_2$, COOH, for the ions, or linkers for the radical addends. The MRI enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in, e.g., Pykett, Scientific American, 246:78 (1982); and Runge et al., Am. J. Radiol., 141:1209 (1987).

It is well understood that many of the same methods for introducing metals, directly or in the form of chelates, into antibodies will be suitable for introduction of MRI agents into the antibody composites of the invention to form imaging agents for infectious lesions. MRI agents advantageously have a large number of paramagnetic ions or radicals for enhanced imaging. One method for introducing a plurality of such ions is to load a carrier polymer with chelates and link the carrier to the antibody composite, preferably site-specifically at a site remote from the antigen binding sites of the composite. This has the advantage that larger numbers of chelators can be attached to the antibody at fewer sites on the antibody itself, so that immunoreactivity is not as seriously compromised. Examples of polymers that are useful for loading the antibody with chelator include, e.g., polyols, polysaccharides, polypeptides and the like. See U.S. Pat. Nos. 4,699,784 (Shih et al) and 4,046,722 (Rowland). One type of polysaccharide is dextran. The chelator can be functionalized to contain reactive groups towards the dextran hydroxyls, e.g., anhydrides, isocyanates or isothiocyanates and the like. Alternatively, dextran can be derivatized in a number of ways, e.g., by conversion to an aminodextran. It will be appreciated that similar methods will be useful for loading a plurality of drug molecules on an antibody or antibody composite, as will be discussed more fully hereinafter.

The process for preparing an antibody conjugate with an aminodextran (AD) carrier normally starts with a dextran polymer, advantageously a dextran of average molecular weight (MW) of about 10,000–100,000, preferably about 10,000–40,000, and more preferably about 15,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like polylysine. A lower number results in less desirable loading of the chelator or boron addend, which may be disadvantageous.

The oxidized dextran is then reacted with a polyamine, preferably a diamine, and more preferably a mono- or poly-hydroxy diamine. Suitable amines include, e.g., ethylenediamine, propylenediamine or similar polymethylenediamines, diethylenetriamine or like polyamines, 1,3-diamino-2-hydroxypropane or other like hydroxylated diamines or polyamines, and the like. An excess of the amine relative to the aldehyde groups can be used, to insure substantially complete conversion of the aldehyde functions to Schiff base (imine) groups.

Reductive stabilization of the resultant intermediate is effected by reacting the Schiff base intermediate with a reducing agent, e.g., $NaBH_4$, $NaBH_3CN$, or the like. An excess of the reducing agent is used to assure substantially complete reduction of the imine groups to secondary amine groups, and reduction of any unreacted aldehyde groups to hydroxyl groups. The resultant adduct can be further purified by passage through a conventional sizing column to remove cross-linked dextrans. An estimate of the primary number of available amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

Alternatively, the dextran can be derivatized by conventional methods for introducing amine functions, e.g., by reaction with cyanogen bromide, followed by reaction with a diamine. The AD should be reacted with a derivative of the particular drug or chelator, in an activated form, preferably a carboxyl-activated derivative, prepared by conventional means, e.g., using dicyclohexylcarbodiimide (DCC) or a water soluble variant thereof.

The scintigraphic imaging method of the invention is practiced by injecting a mammal, preferably a human, parenterally with an effective amount for scintigraphic imaging of the radiolabeled polyspecific anti-leukocyte antibody composite. By parenterally is meant, e.g. intravenously, intraarterially, intrathecally, interstitially or intracavitarily. It is contemplated that a subject will receive a dosage of from about 1 mCi to 50 mCi of radiolabeled conjugate, the amount being a function of the particular radioisotope and mode of administration. For intravenous injection, the amounts are normally: about 2–10 mCi, preferably about 2–5 mCi, of I-131; about 5–10 mCi, preferably about 8 mCi, of I-123; about 10–40 mCi, preferably about 20 mCi of Tc-99m; about 2–5 mCi, preferably about 4 mCi of In-111 or Ga-67.

The radiolabeled polyspecific anti-leukocyte antibody composite is conveniently provided as an injectable preparation for mammalian use, preferably a sterile injectable preparation for human use, for targeting a scintigraphic imaging agent to an infectious or inflammatory lesion containing leukocytes, preferably comprising: a sterile injectable solution containing an effective amount of the radiolabeled composite in a pharmaceutically acceptable sterile injection vehicle, preferably phosphate-buffered saline (PBS) at physiological pH and concentration. Other conventional pharmaceutically acceptable vehicles may be utilized as required for the site of parenteral administration.

A representative preparation to be parenterally administered in accordance with this invention will normally contain about 0.1 to 20 mg, preferably about 2 mg, of radiolabeled polyspecific antibody composite, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride.

Once enough isotope has deposited at the target site, scanning is effected with either a conventional planar and/or SPECT gamma camera, or by use of a hand held gamma probe used externally or internally to localize the inflammation or the lesion. The scintigram is normally taken by a gamma imaging camera having one or more windows for detection of energies in the 50–500 KeV range. The target site can be any infectious lesion, inflammatory deposit or occult lesion having leukocytes present in a relatively concentrated focus. Localization of lesions containing leukocytes will occur directly through reactivity of the polyspecific antibody-agent conjugate with the leukocytes resident in the lesion at the time of parenteral administration as well as through entry of labeled leukocytes into the lesion.

Magnetic resonance imaging (MRI) is effected in an analogous method to scintigraphic imaging except that the imaging agents will contain MRI enhancing species rather than radioisotopes. It will be appreciated that the magnetic resonance phenomenon operates on a different principle from scintigraphy. Normally the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to increase both $T_1$, and $T_2$, the former resulting in greater contrast, while the latter results in lesser contrast. Accordingly the phenomenon is concentration-dependent, and there is normally an optimum concentration of a paramagnetic species for maximum efficacy. The optimum concentration will vary with the particular agent used, the locus of imaging, the mode of imaging, i.e., spin-echo, saturation-recovery, inversion-recovery and for various other strongly $T_1$ dependent or $T_2$ dependent imaging techniques, and the composition of the medium in which the agent is dissolved or suspended. These factors, and their relative importance are known in the art. See, e.g., Pykett, o.p.cit., and Runge et al., op.cit.

The MRI method of the invention is practiced by injecting a mammal, preferably a human, parenterally with an effective amount for magnetic resonance imaging of a conjugate according to the present invention of a polyspecific anti-leukocyte antibody composite and an MRI enhancing agent. It is contemplated that a subject will receive a dosage of labeled conjugate sufficient to enhance the MRI signal at the site of a lesion by at least about 20%, preferably 50–500%, the amount being a function of the particular paramagnetic species and the mode of administration.

Again, the labeled polyspecific anti-leukocyte antibody composite is conveniently provided as an injectable preparation for mammalian use, preferably a sterile injectable preparation for human use, for targeting a MRI agent to an infectious or inflammatory lesion containing leukocytes, preferably comprising: a sterile injectable solution containing an effective amount of the labeled composite in a pharmaceutically acceptable sterile injection vehicle, preferably phosphate-buffered saline (PBS) at physiological pH and concentration. Other conventional pharmaceutically acceptable vehicles for parenteral administration may be utilized as required for the site of parenteral administration.

A representative preparation to be parenterally administered in accordance with this invention will normally contain about 0.1 to 20 mg, preferably about 2 mg, of labeled polyspecific antibody composite, in a sterile solution which advantageously also contains, e.g., about 10 mg of human serum albumin (1% USP: Parke-Davis) per milliliter of 0.04M phosphate buffer (pH 7.4 Bioware) containing 0.9% sodium chloride. Once enough of the MRI agent has deposited at the target site, scanning is effected with a conventional MRI camera camera to image the lesion.

In a preferred embodiment of this invention, the localization ratio of the primary labeled polyspecific antibody-agent conjugate is enhanced through the use of a nonlabeled second antibody to scavenge non-targeted circulating conjugate and promote its clearance, as disclosed for related imaging agents in Goldenberg, U.S. Pat. No. 4,624,846, the disclosure of which is incorporated herein in its entirety by reference. This technique is likewise applicable to the polyspecific anti-leukocyte antibody composite conjugated to a therapeutic drug, as will be discussed hereinafter. The term "localization ratio" is utilized in its conventional sense, i.e. the ratio of target to nontarget antibody conjugate. In general, the second antibody is used in an amount that will enhance the localization ratio of the primary antibody conjugate by at least about 20 percent and typically by 50 percent or more.

The second antibody may be whole IgG or IgM, or a fragment of IgG or IgM, so long as it is capable of binding the primary antibody conjugate to form a complex which is cleared from the circulation and the non-target spaces more rapidly than the primary antibody conjugate by itself. Preferably, the second antibody will be whole IgG or IgM. If the primary antibody is a fragment of IgG or IgM, it is preferable that the second antibody be whole IgG or IgM so that the primary/secondary complex retains the capability of activating the complement cascade. Conversely, where the primary antibody is whole IgG, the second antibody may be a fragment if the complex still retains complement-fixing capability. It is preferred that at least one of the primary/secondary pair be whole IgG or IgM. One advantage of using IgM is that it forms a higher molecular weight complex with primary antibody or with detached conjugates, ie., diagnostic and/or therapeutic principles such as drugs, chelating agents, radionuclides, and the like. This will increase the rate and effectiveness of clearance of non-target primary antibody and/or principle, especially from blood. The second antibody can be prepared by methods disclosed in the aforementioned Goldenberg '846 patent. Monoclonal anti-species IgG is also available and is advantageously used as second antibody in the present process. Non-metallic conjugates, e.g., radio-iodinated linking groups or organic paramagnetic species such as nitroxides, can also be haptens to which the second antibody is specific.

The second antibody is injected into the subject after a sufficient time has elapsed following parenteral administration of the primary polyspecific antibody-agent conjugate to permit maximum uptake thereof by leukocytes, typically about 2–72 hours following the initial administration, preferably at about 24–48 hours post-administration. If the primary antibody is not administered intravenously, it may be advantageous to administer at least a portion of the second antibody by the same parenteral route. It is advantageous however, to inject at least a portion of the second antibody intraveneously to accelerate clearance of primary antibody which has diffused into the circulatory system.

The use of second antibody to clear circulating labeled primary antibody and enhance the localization ratio of the primary antibody is further enhanced by utilization of image-enhancing subtraction techniques as disclosed in the foregoing Goldenberg patents as well as the references cited therein. This is an art-recognized technique wherein an indifferent antibody or fragment labeled with a radionuclide capable of independent detection. This antibody has substantially the same kinetics of distribution and metabolism as the primary antibody during the period required for imaging. The injection of such antibodies is preferred over conventional subtraction agents, such as Tc-99m-labeled serum albumin, which are nevertheless suitable for use to enhance image processing by compensating for background. The use of the radiolabeled indifferent antibody as a subtraction agent permits computerized correction for nontarget background radiation from organs which effect clearance of antibodies from the circulatory system. It will be appreciated by those of ordinary skill in the art that the primary monoclonal antibody and the indifferent antibody utilized as a subtraction agent are preferably from the same species or myeloma/hybridoma so that the second antibody will clear the primary monoclonal antibody and the indifferent antibody immunoglobulin from untargeted areas at substantially the same rate. It is further preferred that the second antibody be specific to a constant region of the primary and indifferent immunoglobulin species.

The amount of second antibody introduced will generally be that amount which can decrease the circulating primary antibody by 10–85% within 2–72 hours. The ratio of second antibody to primary antibody which will affect the clearance will depend upon the binding properties of the primary and secondary antibody pair. Preliminary screening of patient blood in vitro can be used to provide an initial estimate of the appropriate ratio. The screen will be used to determine the ratio of second antibody to primary antibody required to obtain a precipitin band in, e.g., a gel diffusion test. This indicates the general range of the molar ratio of second antibody to primary antibody, which serves as a measure of the lower limit for the ratio, since in vivo application may require a higher ratio of second antibody to primary antibody than is indicated by such in vitro tests.

In practice, the molar ratio of second antibody to primary antibody will generally be in the range of about 5–50, although the range should not be considered limitative. Molar ratios of second antibody to primary antibody of 15–25, and preferably 20–25, have been found to be advantageous where both the primary and the second antibody are whole IgG.

Many drugs are known which have a cytotoxic effect on cells or microorganisms that may infect a human and cause a lesion. They can be found in any of the readily available art-recognized compendia of drugs and toxins, such as the Merck Index and the like. Any such antibiotic drug can be conjugated to an anti-leukocyte antibody or antibody composite to form a therapy agent according to the present invention, and the use of such a conjugate to improve the targeting of an antibiotic drug to the site of an infectious lesion so as to increase its effective concentration at the site is a part of the present invention. One or more antibiotic drugs is/are conjugated to a polymeric carrier which is then conjugated to the antibody or antibody composite, for therapeutic use. In certain cases, it is possible to partially or completely detoxify a drug as part of the antibody conjugate, while it is in circulation, which can reduce systemic side effects of the drug and permit its use when systemic administration of the drug would be unacceptable. Administration of more molecules of the drug conjugated to a polymer which is further conjugated to the antibody, permits therapy while mitigating systemic toxicity.

The methodology of this invention is applicable to the therapeutic treatment of infectious lesions by conjugating the primary antibody or antibody composite to an antibiotic drug. Art recognized methods of conjugating antibiotic drugs to immunoglobulins are described, e.g., in: the chapter by O'Neill, entitled "The Use of Antibodies as Drug Carriers," in Drug Carriers in Biology and Medicine, G. Gregoriadis, ed., Academic Press London, 1979; Arnon et al., Recent Results in Cancer Res. 75:236, 1980; and Moolton et al., Immunolog. Res. 62:47, 1982, showing art awareness. These methods are quite similar to the methods employed for coupling drugs effective against various disease-causing microorganisms, such as against bacteria, viruses, fungi and diverse parasites to antibodies developed against these microorganisms, their products or antigens associated with their lesions.

Such antibaterial, antiviral, antiparasitic, antifungal and related drugs, e.g., sulfonamides, penicillins and cephalosporins, aminoglycosides, tetracyclines, chloramphenicol, piperazine, chloroquine, diaminopyridines, metroniazide, isoniazide, rifampins, streptomycins, sulfones, erythromycin, polymixins, nystatin, amphotericins, 5-fluorocytosine, 5-iodo-2'-deoxyuridine, 1-adamantanamine, adenine arabinoside, amanitins and azidothymidine (AZT), are preferred for coupling to appropriate specific antibodies/fragments and antibody/fragment composites. Various other potential antimicrobial agents for use in this invention are listed in Goodman et al., "The Pharmacological Basis of Therapeutics," Sixth Edition, A. G. Gilman et al., eds., Macmillan Publishing Co., New York, 1098, showing general art awareness. Various conditions appropriate and desirable for targeting drugs to specific target sites have been reviewed e.g. by Trouet et al., in Targeting of Drugs, G. Gregoriadis et al., eds., Plenum Press, New York and London, 1982, pp. 19–30, showing clinical knowledge of how such targeting would benefit patients suffering from infectious lesions.

The use of a second antibody as described above will increase the effectiveness of the therapeutic agent according to the invention in the same manner as for the diagnostic imaging conjugate. The effectiveness of the therapeutic agent is expressed in terms of its therapeutic index which, utilized in the conventional sense, is defined as the ratio of therapeutic effects to undesirable side effects. It is often defined in terms of a quantitative measure of efficacy vs. toxicity in a standard model system, e.g., the ratio of the median lethal dose ($LD_{50}$) to the median effective dose ($ED_{50}$). The use of second antibody as described herein produces an increase in the therapeutic index of anti-leukocyte antibody and antibody composite conjugates by clearing nontarget primary antibody and/or detached therapeutic principle. In addition to being specific to the primary monoclonal antibody as discussed above, in the instance of the therapeutic preparation, the second antibody can be specific to the therapeutic agent. It can also be specific to a carrier for the therapeutic agent.

Therapeutic preparations contemplated herein comprise monospecific anti-leukocyte antibodies/fragments as defined above, conjugated to a therapeutically effective drug, in a suitable vehicle for parenteral administration. A therapeutic preparation may likewise comprise a polyspecific anti-leukocyte antibody/fragment composite conjugated to an antibiotic. Therapeutic preparations may also include a separately packaged second antibody as described above. Suitable vehicles are well know in the art and can include, e.g., analogous sterile PBS solutions to those used for administration of diagnostic imaging agents, as discussed hereinabove.

The anti-leukocyte polyspecific imaging conjugates and monospecific or polyspecific therapeutic conjugates according to the invention also can be conveniently provided in a therapeutic or diagnostic kit for antibody targeting to an infectious or inflammatory lesion containing a focus of leukocytes. Typically, such a kit will comprise: a vial containing the antibody conjugate of the present invention, either as a lyophilized preparation or in an injection vehicle; if the conjugate is to be used for scintigraphic imaging, it will generally be provided as a cold conjugate together with reagents and accessories for radiolabeling, in separate containers, while MRI agents and therapeutic conjugates will generally be supplied with a paramagnetic species or an antibiotic already conjugated to the antibody/fragment composite or monospecific antibody/fragment. The kit may further contain a second, separately packaged, unlabeled antibody or antibody fragment specific against the antibody or fragment or the therapeutic agent, a carrier therefor, or a chelating agent for the radionuclide or paramagnetic ion.

The imaging preparations and methods of this invention are at least as efficacious as the conventional agents for determination of occult abscesses using In-111-labeled leukocytes and are clearly advantageous thereover in terms of cost, potential toxicity of the reagent and, most significant, ease of use. The therpeutic reagents and methods of the invention provide a means to target sites of microbial infection with antibiotic drugs to improve the therapeutic index of the drugs, reduce systemic side effects and enhance their efficacy.

Without further elaboration, it is believed that one skilled in the art can, using the preceding description, utilize the present invention to its fullest extent. The following preferred specific embodiments are therefore, to be construed as merely illustrative, and not limitative of the remainder of the disclosure in any way whatsover. In the following examples, all temperatures are set forth uncorrected in degrees Celsius, unless otherwise indicated, all parts and percentages are by weight.

EXAMPLE 1

Bispecific Anti-leukocyte Composite

A bispecific antibody composite is prepared from a F(ab')$_2$ fragment of a monoclonal antibody highly specific for granulocyte cells. The interchain disulfide bridges are reduced carefully with cysteine, taking care to avoid light-heavy chain cleavage, to form Fab'-SH fragments. The SH group(s) is(are) activated with an excess of bis-maleimide linker (1,1'-(methylenedi-4,1-phenylene)bismaleimide, Aldrich Chemical Co., Milwaukee, Wis.). A second monoclonal antibody, highly specific for an antigen common to B-lymphocyte cells and macrophages (anti-Ia), is converted to Fab'-SH and then reacted with the activated anti-granulocyte fragment to obtain a bispecific composite. The composite can be reacted with 2-iminothiolane to introduce one or more sulfhydryl groups for use in coupling the composite to a third antibody/fragment, using the same bis-maleimide activation procedure described above, or for use in direct metallation with, e.g., Tc-99m from reduced (e.g., with SnCl$_2$) pertechnetate.

EXAMPLE 2

Polyspecific Anti-leukocyte Composite

A polyspecific antibody composite is prepared from a monoclonal antibody specific for T-lymphocytes (anti-T-1), which has been converted to Fab'-SH fragments and activated with bis-maleimide linker, then coupled to the bispecific fragment described above that has been activated by incorporation of an SH group, using 2-iminothiolane. The polyspecific composite is labeled with one of the several radionuclides useful for imaging (Tc-99m, I-123, Ga-67, In-111) for use to detect infectious lesions or inflammatory deposits by RAID.

EXAMPLE 3

Scintigraphic Imaging Kit

A diagnostic imaging kit contains: a first sterile vial fitted with a rubber septum, and containing the thiol-activated polyspecific composite of Example 2, in the form of a lyophilized preparation; a second sterile (septum-sealed) vial containing phosphate-buffered saline, pH 7.4; a third sterile (septum-sealed) vial containing a solution of stannous glucoheptonate for reduction of 99m-pertechnetate; and additional septum-sealed sterile vials and sterile syringes for labeling and injection of the preparation. Optionally, the kit can include a separate sterile vial containing a second antibody for rapid clearance of circulating labeled composite after localization, for example, affinity-purified rabbit anti-mouse antibody.

EXAMPLE 4

Diagnostic Imaging

A 24-year old female patient develops fever and abdominal pain one week after giving birth to a male infant by Caesarean section. The patient is maintained on I.V. antibiotic therapy for two weeks, but the fever and abdominal pain persists. CAT scans fail to demonstrate any abnormal mass. An immunoscintigraphy study is performed using the polyspecific anti-leukocyte composite of Example 2, directly labeled with Tc-99m radioisotope using the kit components of Example 3 and generator-produced sodium pertechnetate. An injection of 20 mCi of radiolabeled composite is used, and the patient is scanned with a gamma camera in SPECT mode. The scan of the patient's abdomen demonstrates a focus of accumulation of Tc-99m. Surgery is performed and an abscess is found at the site of Tc-99m activity. The abscess is drained, and pathology demonstrates large numbers of granulocytes, as well as monocytes, B-lymphocytes and activated T-lymphocytes, present in the purulent material. After two days, the patient's fever and pain subside.

EXAMPLE 5

Diagnostic Imaging

A 58-year old female patient that has been treated for pyelonephritis develops fever and acute spinal tenderness. Vertebral osteomyelitis is suspected, but radiography of the spine is normal. An immunoscintigraphy study is performed using the polyspecific anti-leukocyte composite of Example 2, directly labeled with Tc-99m radioisotope using the kit components of Example 3 and generator-produced sodium pertechnetate. An injection of 20 mCi of radiolabeled composite is used, and the patient is scanned with a gamma camera in planar imaging mode 24 hours after administration of the labeled conposite. The scan shows an intense focus of Tc-99m just above the point of termination of the spinal chord. Laminectomy and drainage of the epidural spaces is performed at the target site. Pathology of the purulent material in the drainage fluid demonstrates primarily exhuberant granulation tissue containing large numbers of mononuclear lymphoid cells with fewer numbers of granulocytes.

EXAMPLE 6

Therapy

A 42-year old male with AIDS presents with bilateral pneumonia which fails to respond to conventional broad-spectrum antibiotic therapy. The clinical presentation and sputum cytology suggest *Pneumocystis carinii* pneumonia which appears to be advanced and to be causing the patient severe respiratory distress. A mixture of monoclonal antibodies which bind to granulocyte and monocyte antigens are each site-specifically conjugated to an average of one aminodextran carrier of about 15,000 MW, bearing an average of about 25 molecules of trimethoprin (Wellcome), a methotrexate derivative conjugated to the carrier by adapting the methodology of the Shih et al. patent cited hereinabove. A slow intravenous infusion of about 25 mg of the antibody conjugate mixture delivers a therapeutic dose of the antibiotic to the pulmonary lesions, and is repeated on each of three successive days. Two days later, the patient begins to show improvement and his fever abates, and this is confirmed by improvement in his chest roentgenograms three days later. Most of the pneumonia resolves within two weeks of the antibody-drug conjugate treatment, with the patient receiving general supportive measures during this time.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A polyspecific anti-leukocyte antibody conjugate for enhanced targeting to leukocyte accretion, comprising at least one antimicrobial therapeutic agent conjugated to an immunoreactive polyspecific composite which specifically binds to at least two types of leukocytes, wherein said composite comprises at least two different substantially monospecific antibodies or antibody fragments which are chemically bound to one another either directly or through one or more linkers.

2. A polyspecific anti-leukocyte antibody conjugate according to claim 1, wherein said at least two types of leukocytes are selected from the group consisting of granulocytes, monocytes, B-lymphocytes and T-lymphocytes.

3. A polyspecific anti-leukocyte antibody conjugate according to claim 1, wherein each said antibody or antibody fragment is monoclonal.

4. A polyspecific anti-leukocyte antibody conjugate according to claim 1, wherein said substantially monospecific antibody fragments are selected from the group consisting of $F(ab')_2$, Fab' and Fab.

5. A polyspecific anti-leukocyte antibody conjugate according to claim 1, wherein least at one of said antibodies or antibody fragments specifically binds to the Ia(DR) antigen.

6. A polyspecific anti-leukocyte antibody conjugate according to claim 1, wherein said therapeutic agent is an antibacterial agent.

7. A polyspecific anti-leukocyte antibody conjugate according to claim 1, wherein said therapeutic agent is an antiviral agent.

8. A polyspecific anti-leukocyte antibody conjugate according to claim 1, wherein said therapeutic agent is an antifungal agent.

9. A polyspecific anti-leukocyte antibody conjugate according to claim 1, wherein said therapeutic agent is an antiparasitic agent.

10. A polyspecific anti-leukocyte antibody conjugate according to claim 1, wherein said different substantially monospecific antibodies or antibody fragments are bound directly to one another.

11. A polyspecific anti-leukocyte antibody conjugate according to claim 8, wherein said different substantially monospecific antibodies or antibody fragments are covalently bound to one another through a linker.

12. A method of treatment of an infectious lesion by enhanced targeting to leukocyte accretion, which comprises injecting a mammal parenterally with an effective amount for therapy of the polyspecific anti-leukocyte antibody conjugate of claim 1.

13. The method of claim 12, further comprising the step of parenterally administering to the subject, at a time after administration of said polyspecific anti-leukocyte antibody conjugate sufficient to permit maximum selective uptake thereof by leukocytes at the site of said lesion, a second, unlabeled antibody or antibody fragment which specifically binds to said polyspecific anti-leukocyte antibody conjugate, in an amount sufficient to increase the therapeutic index of said therapy agent by at least about 10 percent.

14. A sterile injectable preparation for enhanced targeting of an antimicrobial therapeutic agent to an infectious lesion, comprising an effective amount for therapy of the polyspecific anti-leukocyte antibody conjugate of claim 1, in a pharmaceutically acceptable sterile injection vehicle.

15. A kit for use in targeting an infectious lesion by enhanced targeting to leukocyte accretion comprising the polyspecific anti-leukocyte antibody conjugate of claim 1 in a sterile container.

16. The kit of claim 15, further comprising a second, unlabeled antibody or antibody fragment which specifically binds to said polyspecific anti-leukocyte antibody conjugate, said second, unlabeled antibody or antibody fragment being provided in a separate sterile container from said polyspecific anti-leukocyte antibody conjugate.

* * * * *